(12) United States Patent
Gleich

(10) Patent No.: US 7,300,452 B2
(45) Date of Patent: Nov. 27, 2007

(54) METHOD FOR LOCAL HEATING BY MEANS OF MAGNETIC PARTICLES

(75) Inventor: Bernhard Gleich, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 256 days.

(21) Appl. No.: 10/525,170

(22) PCT Filed: Aug. 15, 2003

(86) PCT No.: PCT/IB03/03716

§ 371 (c)(1),
(2), (4) Date: Feb. 22, 2005

(87) PCT Pub. No.: WO2004/018039

PCT Pub. Date: Mar. 4, 2004

(65) Prior Publication Data

US 2006/0009826 A1    Jan. 12, 2006

(30) Foreign Application Priority Data

Aug. 24, 2002 (DE) .............................. 102 38 853

(51) Int. Cl.
*A61F 7/00* (2006.01)
(52) U.S. Cl. ..................... 607/105; 600/9; 600/12; 128/898; 606/27
(58) Field of Classification Search ............ 606/27–31; 607/103; 600/12, 9–15; 219/634; 128/898
See application file for complete search history.

(56) References Cited

U.S. PATENT DOCUMENTS

| | | | | |
|---|---|---|---|---|
| 4,622,952 A * | 11/1986 | Gordon | ...................... | 600/10 |
| 4,662,359 A * | 5/1987 | Gordon | ...................... | 600/10 |
| 4,674,481 A * | 6/1987 | Boddie et al. | ................ | 600/10 |
| 5,622,686 A * | 4/1997 | Gordon et al. | ............. | 424/9.32 |
| 5,658,234 A * | 8/1997 | Dunlavy | ....................... | 600/9 |
| 6,149,576 A * | 11/2000 | Gray et al. | .................... | 600/9 |
| 6,167,313 A * | 12/2000 | Gray et al. | ................ | 607/103 |
| 6,470,220 B1 * | 10/2002 | Kraus et al. | ................ | 607/103 |
| 6,565,887 B1 * | 5/2003 | Gray et al. | ................ | 424/489 |
| 6,575,893 B2 * | 6/2003 | Feucht | ......................... | 600/13 |
| 6,599,234 B1 * | 7/2003 | Gray et al. | .................. | 600/12 |
| 6,635,009 B2 * | 10/2003 | Feucht | ......................... | 600/13 |
| 6,997,863 B2 * | 2/2006 | Handy et al. | .................. | 600/9 |
| 7,074,175 B2 * | 7/2006 | Handy et al. | .................. | 600/9 |
| 2003/0006773 A1 * | 1/2003 | Ries | ......................... | 324/318 |
| 2003/0129763 A1 * | 7/2003 | Chamberlain et al. | ...... | 436/149 |

FOREIGN PATENT DOCUMENTS

DE    199 3 492    5/2001

* cited by examiner

Primary Examiner—Henry M. Johnson, III
Assistant Examiner—Victoria Chen

(57) ABSTRACT

The invention relates to a method as well as to a system for the local heating of a target region of an object by varying the magnetization of magnetic or magnetizable substances. A magnetic field is then generated whose magnetic field strength varies in space in such a manner that a first sub-region (301) of low magnetic field strength and a second sub-region (302) which encloses the first sub-region and has a higher magnetic field strength are formed in the target region. Subsequently, the position in space of the two sub-regions in the target region is varied with a given frequency for so long that the particles are heated to a desired temperature due to frequent variation of the magnetization.

14 Claims, 5 Drawing Sheets

METHOD FOR LOCAL HEATING BY MEANS OF MAGNETIC PARTICLES

Figure 1:
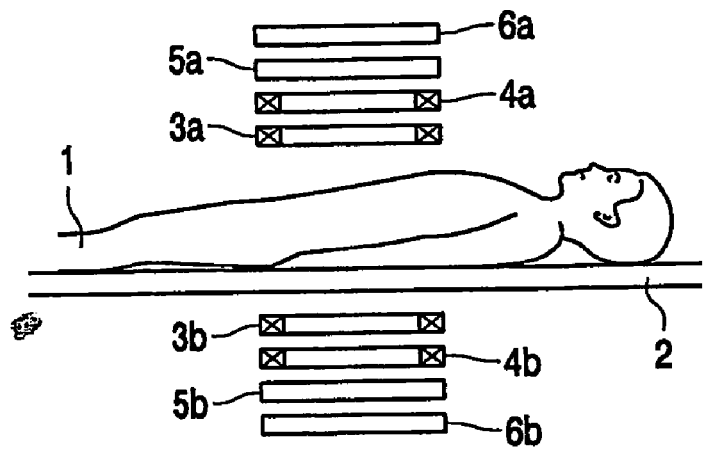

The invention relates to a method and a system for the local heating of regions of an object by variation of the magnetization of magnetic or magnetizable substances.

Methods and systems of this kind are known, for example, from the medical field. In the course of so-called hyperthermia and thermo-ablation operations, diseased tissue is heated to given temperatures so that the tissue mortifies or is destroyed.

A problem generally encountered in hyperthermia consists in that accurately localized and above all homogeneous heating of a region of interest of the body can usually be achieved only with difficulty or only by making a large expenditure on specific hardware. In order to confine the hyperthermia to diseased tissue as well as possible, it is particularly important to confine the heating to the region to be treated.

The publication DE 19937492 discloses a magnetic field applicator for the heating of magnetic or magnetizable substances or solid bodies in parts of an object. The arrangement consists of a magnetic yoke which is made of ferrite components and comprises pole shoes as well as coils wound around the pole shoes. Between the pole shoes there is formed a receiving space in which the object to be treated is to be positioned. The entire receiving space, and hence the entire part of the object situated therein, is traversed by a magnetic alternating field during operation.

It is an object of the invention to provide a method and a system for the heating of an adjustable target region of an object.

This object is achieved by means of a method for the heating of magnetic particles which are present in a target region, which method includes the steps of a) generating a magnetic field whose magnetic field strength varies in space in such a manner that a first sub-region having a low magnetic field strength and a second sub-region having a higher magnetic field strength are formed in the target region, b) changing the position in space of the two sub-regions in the target region for so long and with such a frequency that the target region is heated.

The method in conformity with the invention utilizes magnetic particles which are present in the target region to be heated in the object. Because of its internal structure, the object may permanently contain such particles. Alternatively, such particles can be introduced into the object, for example, by way of a liquid, prior to the heating.

A spatially inhomogeneous magnetic field is generated in the target region. The magnetic field in the first sub-region is so weak that the magnetization of the particles is not saturated. Under the influence of a magnetic field having a given field strength, magnetic particles are not saturated when the magnetization of the particles changes in response to an increase of the field strength of the magnetic field. This first sub-region is preferably a spatially coherent region; it may be a punctiform region but also a line, a surface or a volume. In the second sub-region (that is, in the part of the target region which remains outside the first sub-region) the magnetic field is strong enough to keep the particles in a state of saturation. Under the influence of a magnetic field, magnetic particles are saturated if the change of their magnetization in response to an increase of the magnetic field strength is clearly less in comparison with the response in the non-saturated state.

The state of saturation is dependent on the type of magnetic particles used and is generally imposed by their physical structure or solid state structure. The magnetization is saturated, for example, when the magnetization of practically all particles is oriented approximately in the direction of the external magnetic field (second sub-region), so that in response to a further increase of the magnetic field the magnetization at that area increases significantly less than in the first sub-region in response to a corresponding increase of the magnetic field. For other magnetic particles the state of saturation is reached when the respective magnetization is oriented in the direction of the external magnetic field for a predominant number of inner magnetic regions.

When the position in space of the first sub-region is changed slightly, the magnetization changes of those particles which are situated in the first sub-region or which migrate from the first to the second sub-region or vice versa. Because of this change of the magnetization, heat losses occur, for example, due to known hysteresis effects or hysteresis-like effects in the particles or due to the initiation of particle movements, and the temperature of the medium surrounding the particles is heated in a heating region. When the first sub-region of the magnetic field is shifted through the entire target region, the heating region will correspond to the target region. The smaller the first sub-region, the smaller the size of the smallest possible heating region will be.

Because only a comparatively small amount of heat is produced when the magnetization is changed only once, the magnetization must be changed several times. The necessary number of changes, that is, the frequency within a given time interval, and the associated temperature rise of the medium surrounding the particles in the heating region is dependent on the particle concentration, on the production of heat per change (which itself is dependent on the particle structure and the speed of the magnetic reversal), and the dissipation of heat in the regions surrounding the heating region.

Further advantages over methods which are known from the state of the art result from the use of two sub-regions with different magnetic fields, where the first sub-region with a low field strength is situated within the second sub-region with a higher field strength and the magnetic field of the second sub-region traverses the entire target region. When the target region constitutes a small part of an object, the magnetic field of the second sub-region can also traverse regions of the object which surround the target region or the entire object. The shift of the first sub-region which is necessary for the heating then takes place exclusively within the target region, so that even though the field strength of the magnetic field of the first sub-region changes in the regions outside the target region, the magnetization of the particles does not change. It is thus advantageously achieved that the regions surrounding the target region are not heated, because the magnetic particles present therein are in the saturated state. Moreover, it is not necessary either to position the magnetic particles exclusively in the target region in order to avoid heating of surrounding regions. This is advantageous for medical applications in which the magnetic particles reach, for example, the target region via the blood stream and hence are also present in the surrounding regions.

As a result of a small size of the first sub-region it can be achieved that an almost arbitrarily shaped target region can be heated by way of a grid-like variation of the position in space of the first sub-region. The smaller the first sub-region, the finer the gridding may be and hence the more arbitrary the shape of the region of interest may also be. Furthermore, the target region can be subdivided into various sub-regions, each of which receives a different amount of heat. When the sub-regions consist of similar materials, they will be heated to a different extent. When the sub-regions consist of different materials, the entire target region can be practically homogeneously heated by specific adaptation of the respective heating of the sub-regions. To this end, for example, the frequency or the duration of the heating of the relative sub-regions can be adapted. Alternatively, in order to achieve more effective heating, the target region can deliberately be heated inhomogeneously (for example, outer regions stronger than inner regions).

One possibility for changing the position in space of the two sub-regions consists in displacing a coil system and/or a permanent magnet system (or parts thereof) for generating the magnetic field on the one hand or the object with the region to be heated on the other hand relative to one another. This is a preferred method when very small objects are treated by means of very strong gradients and the frequency required for heating is low. Claim 2, however, describes a preferred embodiment which does not require mechanical movements. The position in space of the two sub-regions can then be changed comparatively quickly; this offers additional advantages in the production of heat and enables high frequencies.

Magnetic particles that are suitable for the method in conformity with the invention should have dimensions which are small in comparison with the size of the regions to be heated by means of the method in accordance with the invention. Furthermore, the magnetization of the particles should reach the saturated state in response to as low as possible field strengths of the magnetic field. The lower the field strength required for this purpose, the less the heating per change of the magnetization will be, but the higher the spatial resolution will be or the weaker the (external) magnetic field to be generated in the target region has to be. When the method is used for medical examinations, moreover, it is important that the particles are not toxic.

In the embodiment disclosed in claim 3 the particles are so small that only a single magnetic domain (monodomain) can be formed within such a particle or that no Weiss regions can arise. The dimensions of the particles should then be in the nanometer range. Particles of this kind are used, for example, in contrast media for MR (=magnetic resonance) examinations. Such particles have a size of from 5 to 10 nm. When the dimensions of the particles are larger, smaller field strengths may suffice to ensure saturation of the magnetization of the particles. However, the dimensions should not be so large that a plurality of magnetic domains or Weiss regions can be formed in the particles. For particles known at present, therefore, suitable particle sizes are in a range of from 2 nm to approximately 800 nm, the upper limit also being dependent on the material. A material that is suitable for monodomain particles is, for example, magnetite ($Fe_3O_4$). The indication of the particle size is given merely by way of example, since the material properties are more important in this context.

The embodiment disclosed in claim 4, however, utilizes larger particles in which a number of magnetic domains may be formed. With a view to the spatial resolution, these particles should consist of a magnetic material which enters the saturated state in response to a low magnetic field strength (implying a low saturation induction). This condition can be dispensed with in the further embodiment disclosed in claim 5. Because the particles then comprise only a thin layer of a magnetic material, magnetic saturation is ensured at a low field strength even if the layer does not consist of a material having a low saturation induction.

The embodiment disclosed in claim 6 enables the particles to be applied in a simple manner in the case of medical examination. When use is made of a dispersion with the monodomain particles in conformity with claim 3, this dispersion can be injected into the blood stream so as to achieve a concentration of particles in the tissue to be heated. Such dispersions are not toxic and are known to be used for contemporary magnetic hyperthermia methods and thermo-ablation methods as well as for the previously mentioned contrast enhancement in MR methods. In the case of MR methods the particles are so small (from 5 to 10 nm) that no Weiss regions can be formed therein.

A dispersion with the particles defined in claim 4 or 5 can be used, for example, after a patient to be examined has orally taken this dispersion, for the heating of selected regions of the gastrointestinal tract or, for example, by injection into the blood stream or directly into the tissue to be treated, for the heating of tumor tissue.

Generally speaking, it is advantageous when the particles have a low effective anisotropy (in this context and hereinafter the term "effective anisotropy" is to be understood to mean the magnetic anisotropy resulting from the shape anisotropy and from the crystal anisotropy), because a change of their magnetization direction does not require a rotation of these particles, so that quickly changing magnetic fields can also be used. However, in the embodiment disclosed in claim 6 use is made of the fact that in the case of particles having a sufficiently large effective anisotropy (for example, elongate particles) a change of the magnetization direction implies a mechanical rotation of the particles which can also be used for the generating of heat.

The heat released when the magnetization of the magnetic particles is frequently changed is due to various effects. In the case of particles with a plurality of Weiss regions heat is produced in known manner by the hysteresis effect where Weiss regions are directed, against molecular forces, out of the natural states of equilibrium. The contribution per magnetizable unit of volume is then proportional to the surface area enclosed by the hysteresis loop when the flux density is plotted as a function of the field strength of the magnetic field. The generation of heat can be attributed to other effects, that is, so-called hysteresis-like effects, notably in the case of small particles with a monodomain. As opposed to the previously mentioned hysteresis effects, such hysteresis-like effects usually occur only in the case of rapidly changing magnetic fields.

It is to be noted that nowadays a large number of magnetic particles of different shapes are known; their shape may be independent from the heating mechanisms. In addition to spherical particles there are, for example, needle-shaped particles which usually comprise a plurality of magnetic domains and exhibit a pronounced mechanical rotation under the influence of a magnetic field for alignment. Furthermore, flat, lens-shaped particles are known in which the magnetization can rotate within one plane only. For further shapes in this respect reference is made to relevant technical literature.

An embodiment as disclosed in claim 7 imparts special adhesion properties to the magnetic particles, so that a very specific concentration in space of the particles is stimulated notably in special tissues.

The kind of particle in conformity with claim 8 is particularly advantageous in order to avoid excessive heating of the target region. When the temperature of a magnetic particle exceeds the Curie temperature, the magnetization of the particle no longer changes despite a correspondingly changing magnetic field. Consequently, these particles do not produce heat. When the temperature drops below the Curie temperature again, the particle responds once more to the magnetic field and heat is produced again. With a view to the respective planned use, the Curie temperature can be taken into account already for the selection of the materials for the particles. This is of importance, for example, for hyperthermia where diseased tissue is heated to temperatures beyond 41° C., but where excessive heating should be avoided because, for example, surrounding, healthy tissue would also be damaged by transfer of heat. In the case of thermo-ablation temperatures beyond 47° C. are pursued for acute cell destruction, but in this case excessive temperatures again lead to detrimental side effects.

An arrangement for carrying out the method in accordance with the invention is disclosed in claim 9. In conformity with claim 10 a gradient field can be generated by means of permanent magnets. In the region between two poles of the same polarity there is formed an inhomogeneous magnetic field which comprises a small first sub-region of low field strength which is surrounded by a second sub-region of higher field strength. The magnetization is not saturated only for the particles which are present in the region around the zero point of the field (first sub-region). The magnetization is in the state of saturation for the particles outside this region.

In order to make the gradient field switchable, in conformity with claim 11 there is provided a gradient coil system for generating a gradient field in the target region which is similar to the previously described magnetic field. If the gradient coil system comprises, for example, two similar windings which are situated to both sides of the target region but are traversed by opposed currents (Maxwell coil), this magnetic field is zero at a point on the winding axis and increases substantially linearly with an opposed polarity to both sides of this point. In the further embodiment in accordance with claim 12 the region produced by the gradient coil arrangement around the zero point of the field, that is, the first sub-region, is shifted within the target region by the temporally variable magnetic field. When the variation in time and the orientation of this magnetic field are suitably chosen, the zero point of the field can traverse the entire target region in this manner.

The local heating will be faster as the frequency at which the position of the zero point of the field in the target region is changed is higher, that is, the faster the temporally variable magnetic field superposed on the magnetic gradient field changes. However, from a technical point of view it is difficult to generate a temporally variable magnetic field whose amplitude suffices to shift the zero point of the field to each point of the target region on the one hand and whose frequency of change is high enough to produce fast heating on the other hand. This problem is mitigated by the embodiment disclosed in claim 13 in which three magnetic fields which are variable at a different speed and with a different amplitude are generated, that is, preferably by means of three coil arrangements. It is a further advantage that the frequencies of the field variations may be so fast (for example, >20 kHz) that they are beyond the limits of human hearing and hence the additional burden on a patient is reduced. The further embodiment disclosed in claim 14 enables the displacement of the field-free point in a three-dimensional region.

Thus far examples were taken from the medical field so as to illustrate the invention. However, generally speaking, it is also possible to use the method in accordance with the invention wherever magnetic particles can be introduced into regions of an object to be heated and the object can be treated by means of magnetic fields.

Figure 2:
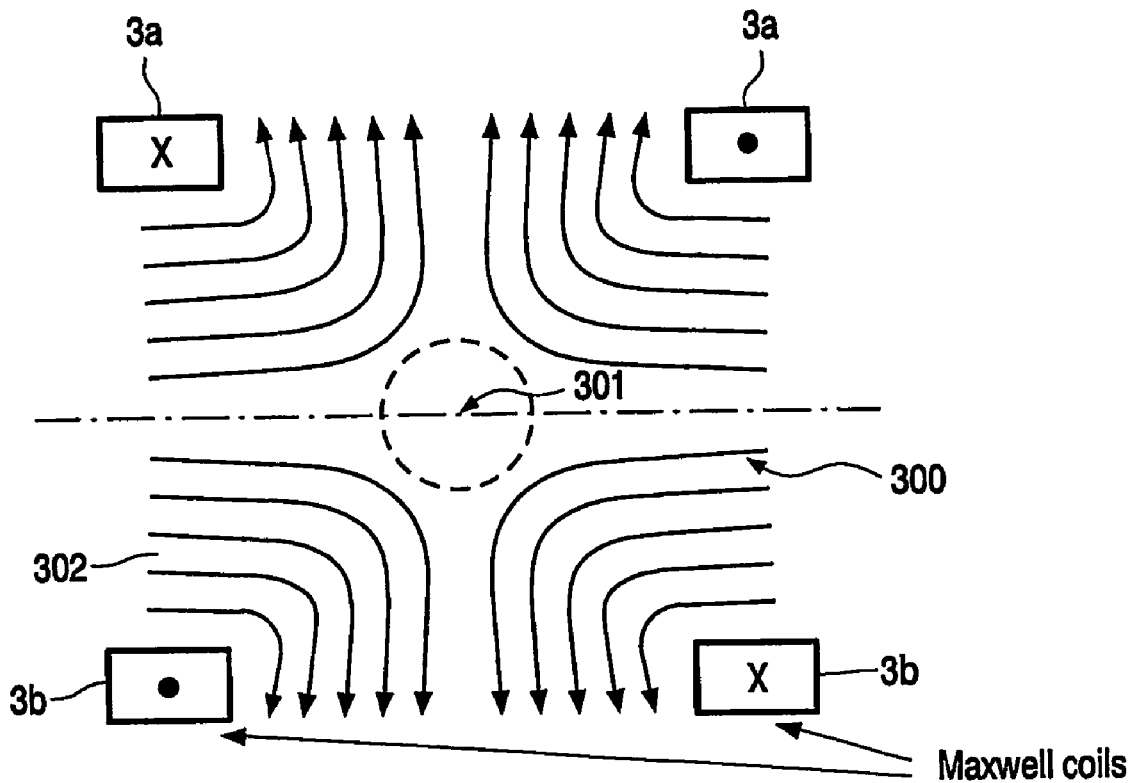
Figure 3:
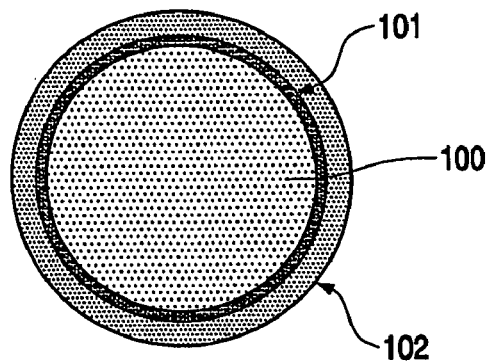
Figure 4A:
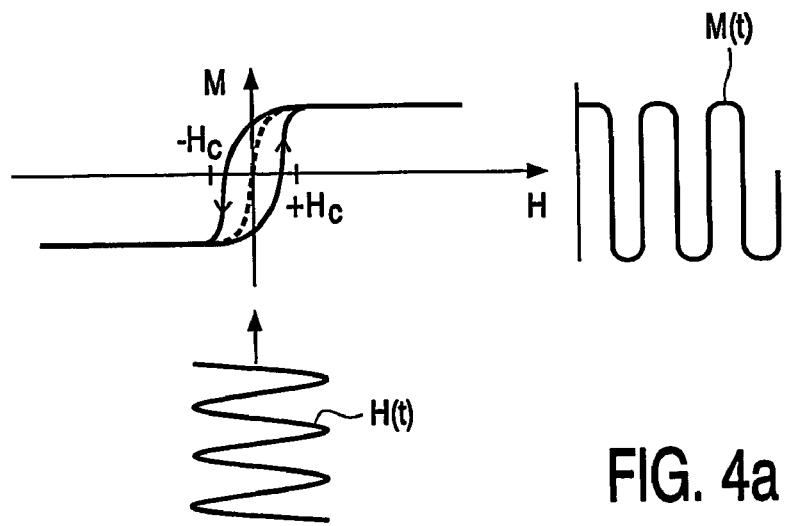
Figure 4B:
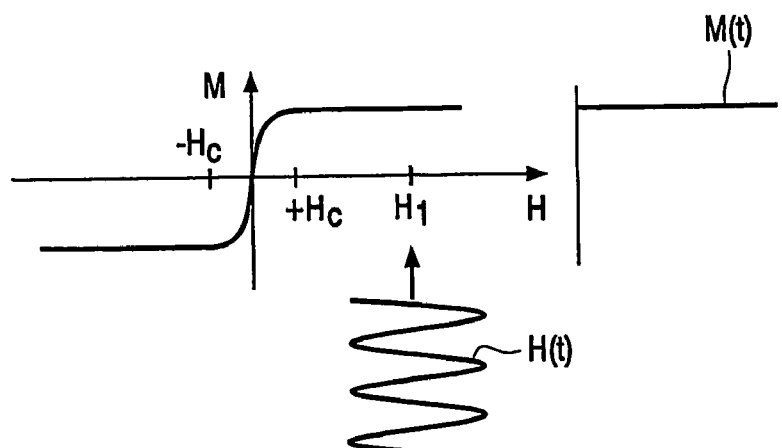
Figure 4C:
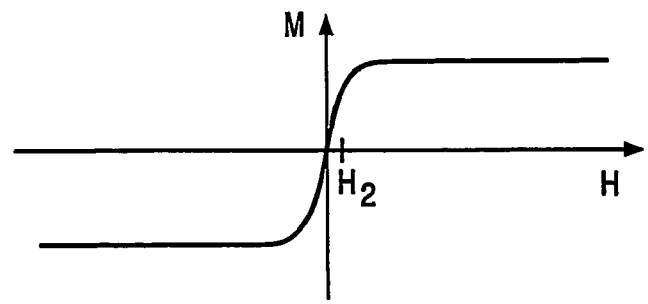
Figure 4D:
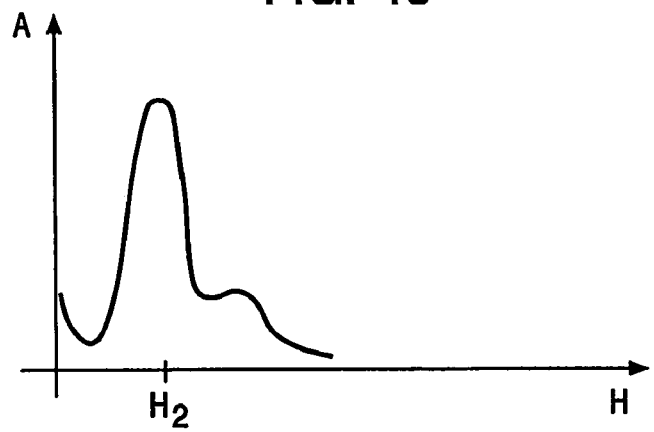
Figure 4E:
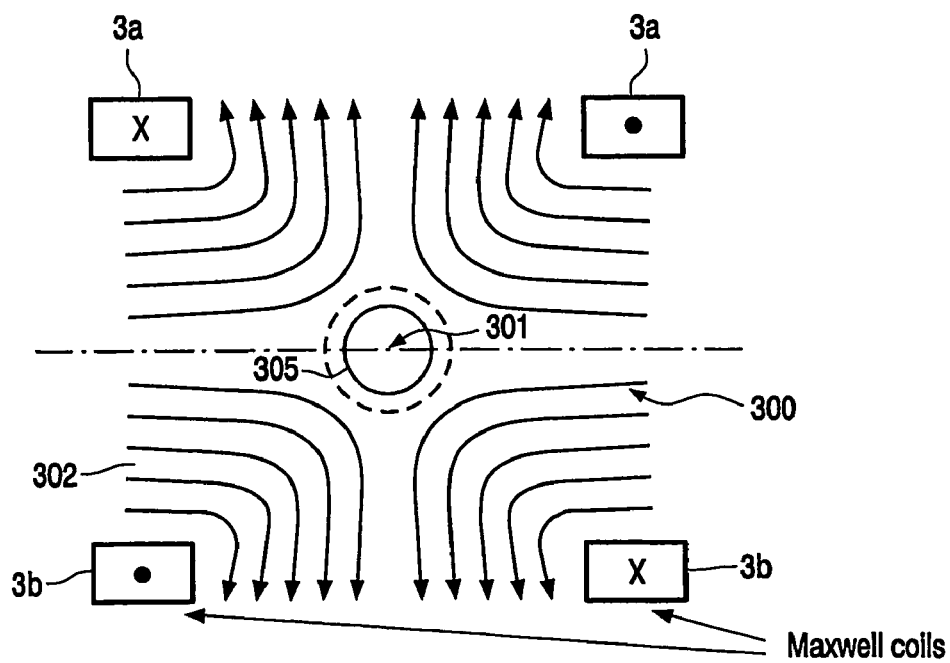
Figure 5:
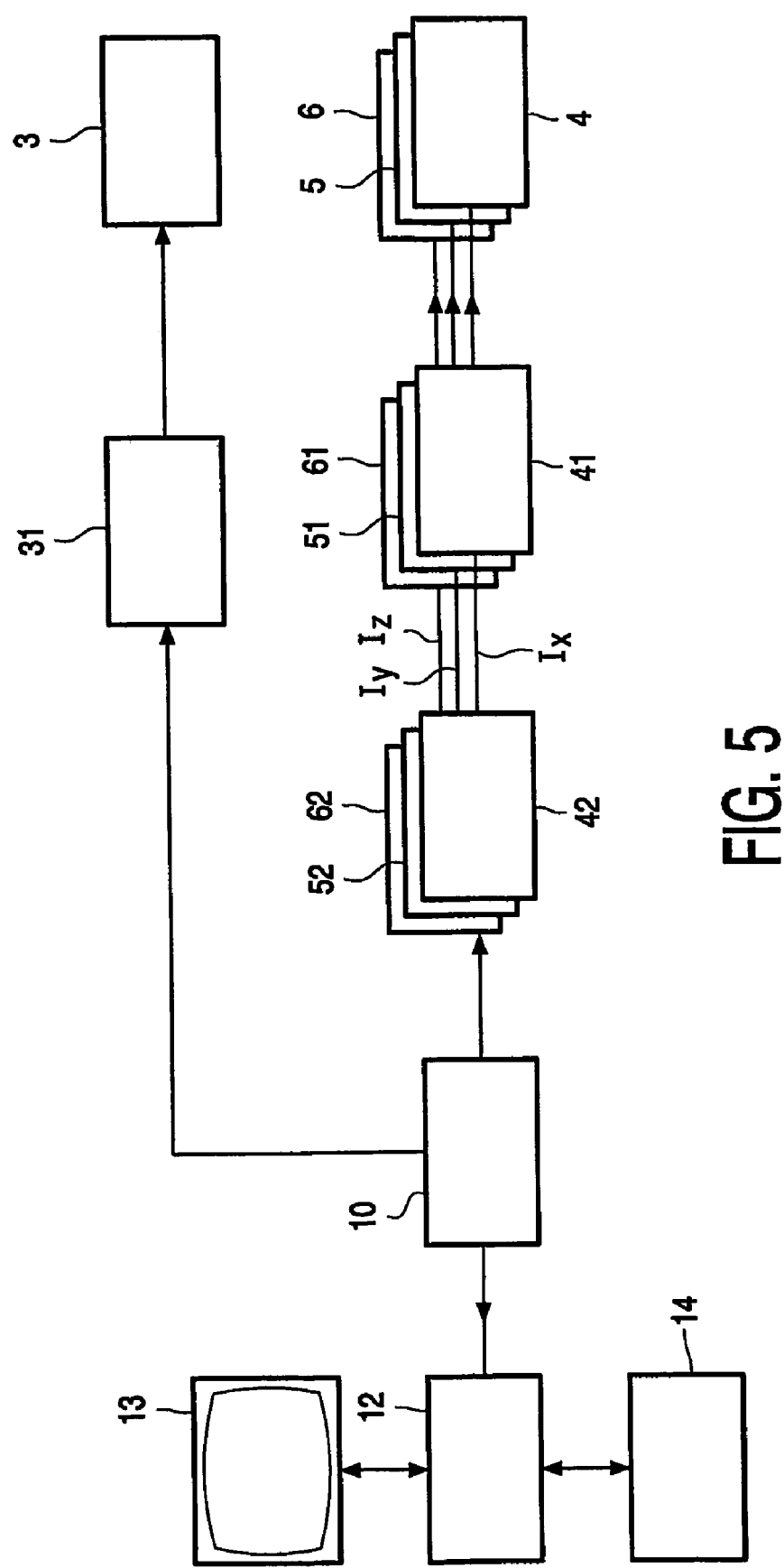
Figure 6:
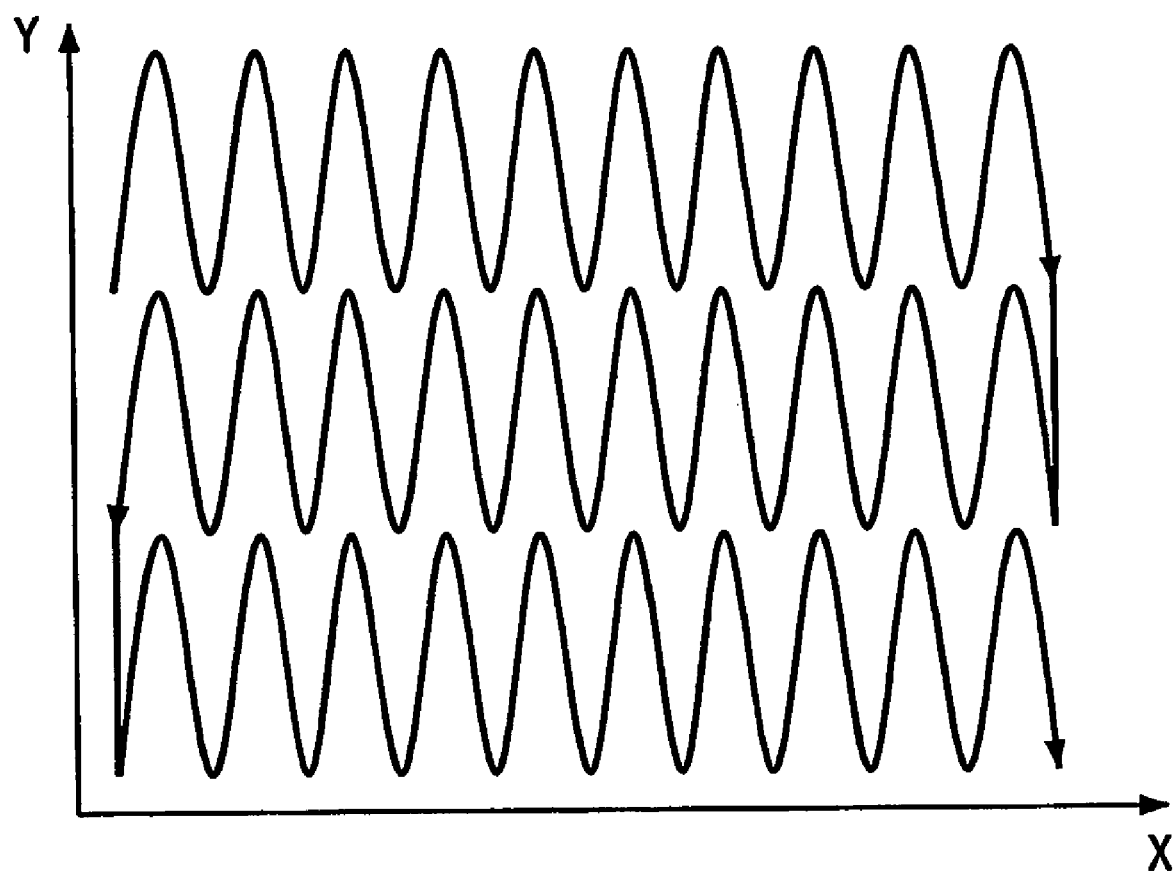

The invention will be described in detail hereinafter with reference to drawings. Therein:

FIG. 1 shows an apparatus for carrying out the method in accordance with the invention, FIG. 2 shows the field line pattern produced by one of the coils included therein, FIG. 3 shows a magnetic particle present in the target region, FIGS. 4a to 4c show the magnetization characteristics of such particles, FIGS. 4d and 4e show the field strength dependent heating of given particles and their positions in the magnetic field, FIG. 5 shows a circuit diagram of the apparatus shown in FIG. 1, and FIG. 6 shows the shift of the field-free point in a two-dimensional region.

The reference numeral 1 in FIG. 1 denotes an object, in this case being a patient, who is arranged on a patient table, only part of the top 2 of which is shown. Prior to a treatment of, for example, a tumor, a liquid with magnetic particles is injected into the patient 1.

FIG. 3 shows a particle of this kind. It comprises a spherical substrate 100, for example, of glass which is provided with a soft-magnetic layer 101 which has a thickness of, for example, 5 nm and consists, for example, of an iron-nickel alloy (for example, Permalloy). This layer may be covered, for example, by means of a coating layer 102 which protects the particle against acids. The strength of the magnetic field required for the saturation of the magnetization of such particles is dependent on the diameter of the particles. In the case of a diameter of 10 μm, a magnetic field of approximately 800 A/m (corresponding approximately to a flux density of 1 mT) is then required, whereas in the case of a diameter of 100 μm a magnetic field of 80 A/m suffices. Even smaller values are obtained when a coating of a material having a lower saturation magnetization is chosen or when the layer thickness is reduced.

FIGS. 4a and 4b show the magnetization characteristic, that is, the variation of the magnetization M as a function of the field strength H, in a dispersion with such particles. It appears that the magnetization M no longer changes beyond a field strength $+H_C$ and below a field strength $-H_C$, which means that a saturated magnetization is involved. The magnetization is not saturated between the values $+H_C$ and $-H_C$.

FIG. 4a illustrates the effect of a sinusoidal magnetic field H(t) if no further magnetic field is active. The magnetization reciprocates between its saturation values at the rhythm of the frequency of the magnetic field H(t). The resultant variation in time of the magnetization is denoted by the reference M(t) in FIG. 4a. It appears that the magnetization also changes periodically and that the magnetization of such a particle is periodically reversed.

The dashed part of the line at the center of the curve denotes the approximate mean variation of the magnetization as a function of the field strength. As a deviation from this center line, the magnetization extends slightly to the right when the magnetic field H increases from $-H_C$ to $+H_C$ and slightly to the left when the magnetic field H decreases from $+H_C$ to $-H_C$. This known effect is called a hysteresis effect which underlies a mechanism for the generation of heat. The hysteresis surface area which is formed between the paths of the curve and whose shape and size are dependent on the material, is a measure for the generation of heat upon variation of the magnetization.

FIG. 4b shows the effect of a sinusoidal magnetic field H(t) on which a static magnetic field $H_1$ is superposed. Because the magnetization is in the saturated state, it is practically not influenced by the sinusoidal magnetic field H(t). The magnetization M(t) remains constant in time at this area. Consequently, the magnetic field H(t) does not cause a change of the state of the magnetization and does not give rise to heat. The hysteresis curve is not shown herein.

Above and below the patient 1 or the table top there is provided a plurality of pairs of coils whose range defines the region of treatment (FIG. 1). A first coil pair 3 comprises the two identically constructed windings 3a and 3b which are arranged coaxially above and below the patient and which are traversed by equal currents, be it in opposed directions. Preferably, direct currents are used in this case. The gradient magnetic field thus generated is represented by the field lines 300 in FIG. 2. It has a substantially constant gradient in the direction of the (vertical) axis of the coil pair and reaches the value zero in a point on this axis. Starting from this field-free point, the strength of the magnetic field increases in all three spatial directions as the distance increases. In a region 301 which is denoted by a dashed line (the first sub-region) around the field-free point the field strength is so small that the magnetization of particles present at that area is not saturated, whereas it is in a state of saturation outside the region 301. In the region remaining outside the region 301 (the second sub-region 302) the magnetization of the particles is in the state of saturation.

The size of the region 301 is dependent on the one hand on the strength of the gradient of the gradient magnetic field and on the other hand on the strength of the magnetic field required for saturation. The field strength of this magnetic field amounts to, for example, 800 A/m for a diameter of 10 μm of the sphere shown in FIG. 3 and to 80 A/m for a diameter of 100 μm. For the latter value and a gradient of the field strength of the magnetic field amounting to $160 \cdot 10^3$ A/m$^2$ the region 301 in which the magnetization of the particles is not saturated has dimensions of 1 mm.

When a further magnetic field is superposed on the gradient magnetic field in the region of treatment, the region 301 is shifted in the direction of this magnetic field; the extent of this shift increases as the strength of the magnetic field increases. When the superposed magnetic field is variable in time, the position of the region 301 varies accordingly in time and in space.

In order to generate these temporally variable magnetic fields for any direction in space there are provided three further coil pairs. The coil pair 4 with the windings 4a and 4b generates a magnetic field which extends in the direction of the coil axis of the coil pair 3a, 3b, that is, vertically. To this end the two windings are traversed by equal currents in the same direction. The effect that can be achieved by means of this coil pair can in principle also be achieved by the superposition of currents in the same direction on the opposed, equal currents in the coil pair 3a, 3b, so that the current decreases in one coil pair and increases in the other coil pair. However, it may be advantageous when the temporally constant gradient magnetic field and the temporally variable vertical magnetic field are generated by separate coil pairs.

Two further coil pairs, comprising the windings 5a, 5b and 6a, 6b, are provided in order to generate magnetic fields which extend horizontally in space in the longitudinal direction of the patient and in a direction perpendicular thereto. If coil pairs of the Helmholtz type, like the coil pairs 3a, 3b and 4a, 4b, were used for this purpose, these coil pairs would have to be arranged to the left and the right of the region of treatment or in front of and behind this region, respectively. This would affect the accessibility of the region of treatment.

Therefore, the windings 5a, 5b and 6a, 6b of the coil pairs are also arranged above and below the region of treatment and, therefore, their winding configuration must be different from that of the coil pair 4a, 4b. Coils of this kind, however, are known from the field of magnetic resonance apparatus with open magnets (open MRI) in which an RF coil pair is situated above and below the region of treatment, said RF coil pair being capable of generating a horizontal, temporally variable magnetic field. Therefore, the construction of such coils need not be further elaborated herein.

As an alternative for the coil pair 3 shown in FIG. 1, permanent magnets can also be used to generate the gradient magnetic field. In the space between two poles of permanent magnets there is formed a magnetic field which is similar to that of FIG. 2, that is, when the poles have the same polarity.

FIG. 5 shows a circuit diagram of the apparatus shown in FIG. 1. The diagrammatically represented coil pair 3 (the indices a, b have been omitted for the sake of simplicity for all coil pairs in FIG. 5) receives a direct current from a controllable current source 31, which current can be controlled and switched on and off by the control unit 10. The control unit 10 co-operates with a workstation 12 via which a user can operate the apparatus and via which the apparatus can be connected to a network of further computers. Depending on its capabilities, the control unit 10 or other components of the apparatus may also be integrated in the workstation 12. User input is possible via a keyboard or another input device 14.

The coil pairs 4, 5, 6 receive their currents from current amplifiers 41, 51 and 61. The variation in time of the currents Ix, Iy and Iz to be amplified, producing the desired magnetic fields, is imposed by a respective waveform generator 42, 52 and 62, respectively. The waveform generators 42, 52, 62 are controlled by the control unit 10 which calculates the variation in time of the currents required for the relevant treatment and loads it into the waveform generators. During the treatment these signals are read from the waveform generators and applied to the amplifiers 41, 51, 61 which form the currents required for the coil pairs 4, 5 and 6 therefrom.

For particles which contribute to the heating due to mechanical motion, a value of, for example, $$130 \, \frac{\text{Hz m}}{\text{A}}$$

can be used as a target value for the frequency of the magnetic field variation (for the particles shown in FIG. 3, for example, frequencies of $$25 \, \frac{\text{kHz m}}{\text{A}} \text{ or } 250 \, \frac{\text{kHz m}}{\text{A}}$$

can be used in dependence on the layer properties), so that a frequency of approximately 1 MHz is obtained for a field strength of the magnetic field of $$8 \cdot 10^3 \; \frac{A}{m}$$

as required for complete magnetic reversal. This frequency is imposed on one of the three coil pairs 4, 5 or 6, for example, the coil pair 4, so that the target region is influenced by an alternating field and the magnetic field region 301 is continuously shifted in a rapidly oscillating fashion in the direction of the magnetic field of the coil pair 4. As a result, a quasi-one-dimensional region of a length which can be adjusted by way of the amplitude of the corresponding coil current is heated as a target region in the treatment region (in the case of a spherical shape of the region 301, an elongate cylindrical region is obtained instead of the strip). The total heating power applied to this strip is dependent inter alia also on the frequency and the amplitude of the alternating field (given by the length in space of the strip), as well as on the field strength required for the maximum development of heat (for example, saturation field strength). The higher the frequency, the higher the heating power will be. The rapidly oscillating magnetic field region 301 is moved in the other dimension by means of the other two coil pairs 5 and 6, so that the entire target region is heated.

FIG. 6 shows the superposition of the individual magnetic fields by way of example. The region 301 is shifted rapidly in the y direction in an oscillating fashion, the shift being due to the periodically varying magnetic field of the coil pair 4. For a better representation, the frequency of the magnetic field generated by the coil pair 4 is shown to be significantly lower, that is, in comparison with the frequencies of the other field, than is actually the case in practice.

The field of the coil pair 5 which varies comparatively slowly in comparison with the field in the y direction is superposed on this field in the x direction. When a given position is reached in the x direction, the shift in the x direction is reversed (the region 301 is thus shifted backwards), and at the same time the field in the y direction is varied by a constant amount, so that the two-dimensional shift of the region 301 through the target region as shown in FIG. 7 is obtained as the part of the treatment region to be heated. If the constant amount is significantly smaller, only a small shift of the field will occur in the y direction, so that because of overlaps the region 301 will cover a point in the target region repeatedly. If a further component is superposed on this field after each scan of the two-dimensional region, that is, a component which shifts the magnetic field in the z direction (corresponding to the magnetic field of the coil pair 6), the region 301 can be shifted through a three-dimensional target region.

Generally speaking, a non-linear relationship exists between the shift of the region 301 from its position at the center of the gradient coil arrangement 3 and the current through the gradient coil arrangement. Moreover, all three coils must generally generate a magnetic field if the region 301 is to be shifted along a straight line extending outside the center (for example, in the case of a grid-like shift through the target region). The foregoing is taken into account by the control unit in selecting the variation in time of the currents, for example, by means of appropriate tables. Therefore, the region 301 can be shifted along arbitrarily formed paths through the examination zone, so that the above displacement of a rapidly oscillating strip is to be considered merely as an example.

For given applications it may be useful to heat only a punctiform or spherical region instead of a one-dimensional strip and to displace this punctiform region in all three spatial directions. This can be realized, for example, by means of a fifth coil pair which is not shown in the Figures and which shifts the first sub-region 301 in a rapidly oscillating fashion in space exactly so far that practically only particles which are located in and around the sub-region 301 contribute to the heating. Alternatively, a corresponding alternating field can also be generated by one or more of the coil pairs 4, 5 or 6, at the same time corresponding, slowly varying magnetic fields being superposed for the displacement in space of the sub-region 301. The configuration in space and in time of the rapid oscillation is dependent on the particles used.

Furthermore, the temperature of the target region can be determined during the treatment by means of components which are not shown. This can be realized, for example, by means of a temperature sensor which is introduced into the target region prior to the treatment. Alternatively, known microwave methods can also be used. In order to prevent overheating, the frequency can be dynamically adapted during the heating, that is, in dependence on the measured temperature. For example, in order to slow down the temperature rise the frequency is decreased more and more as the temperature increases. If no means for temperature measurement are used, the parameters concerning frequency and duration are selected on the basis of the user's experience.

Instead of using the magnetic particles with a soft-magnetic coating as described with reference to FIG. 3, so-called monodomain particles of a ferromagnetic material or a ferrimagnetic material can be used. These particles have dimensions in the nanometer range and are so small that no magnetic domains or Weiss regions can be formed therein. Such particles can be injected into the blood stream of a patient in a suitable colloidal dispersion. Dispersions of this kind are already injected as a contrast medium in the field of magnetic resonance imaging. The magnetic particles used in that field have a size of from 5 to 10 nm. The magnetic field strength required for the saturation decreases by $1/d^3$, where d is the particle diameter. Therefore, the dimensions of these particles should be as large as possible, but not so large that magnetic domains can be formed therein. Depending on the relevant magnetic material, the optimum value is between 2 and 800 nm.

FIG. 4c shows an example of the variation of the magnetization of such a particle in the case of a slowly varying magnetic field H. As opposed to the particles shown in FIG. 3, in this case no hysteresis loop is formed, or only a very small one. However, if the magnetic field H varies rapidly, heat is produced due to the previously mentioned hysteresis-like effects, for example, due to the Néel rotation (damped spin dynamics as well as anisotropies in the molecular composition), due to the rotation of the particles in the surrounding medium or due to the ferromagnetic resonance. Because these effects are known, they will not be elaborated herein and reference is made to the relevant technical literature.

In given types of such particles a particularly large amount of heat is produced when the magnetic field is not varied in the entire range between the two field strengths $-H_C$ and $+H_C$ required for saturation, but only in a small range. FIG. 4d shows, by way of example, the amount of heat A generated in dependence on the magnetic field H for such a particle, on each field strength H there being additionally superposed a rapidly oscillating alternating field H(t) of an amount ΔH which is very small in comparison with the field strength H, so that an overall field amounting to H=$H_{const}$±ΔH is obtained. In comparison with $H_{const}$, the field strength ΔH is so small that it cannot be depicted in FIG. 4d. In FIG. 4d the generating of heat is the greatest in the case of a field strength H=$H_2$±ΔH under the influence of the alternating field ΔH. In addition to the amplitude, the selection of the frequency of the alternating field ΔH is dependent to a high degree on the composition of the particles and may range from a few hundred Hz to as far as the microwave range.

It follows therefrom that when the first sub-region is shifted, a particle of this kind generates most heat when the region of the first sub-region, having the field strength $H_2$, traverses the particle. For the purpose of illustration FIG. 4e shows the gradient field of FIG. 2 with the first sub-region 301. The line 305 characterizes a region with the field strength $H_2$. When the region 301 is shifted only very little in space and in a rapidly oscillating fashion around the co-ordinate zero point shown, an alternating field is superposed (notably on the region with the field strength $H_2$) and the particles located in the vicinity off or on the line 305 produce most heat. The particles located remotely within the line 305 then hardly contribute to the generation of heat, because the field strength H in the region is smaller than $H_2$ and only little heat is produced for such a field strength in conformity with FIG. 4d. In this case the configuration of the magnetic field within the line 305 is of secondary importance only and, as opposed to the situation shown, the field strength need not absolutely necessarily become zero. In dependence on the path traveled during the rapid shift in space and/or on the hysteresis-like effect causing the development of heat, it may occur that the particles contributing to the heating are not located in a coherent sub-region around the line 305 as shown in FIG. 4e, but in a plurality of sub-regions of the first sub-region 301 which are separated from one another.

For magnetic particles it is to be noted that they become concentrated to a different degree in different types of tissue. This effect can be used for specific positioning of the magnetic particles and hence for the local heating and can be intensified by enclosing the particles by means of a coating of organic molecules which enhance the bio-compatibility and have given adhesion properties so as to be concentrated on or in given biological structures. In the ideal case the concentration of the particles takes place only in the parts of the tissue to be treated, so that on the one hand the risk of accidental heating of neighboring parts of the tissue is reduced and on the other hand the requirements as regards the precision of the shift in space of the first sub-region are mitigated.

The heating of the target region beyond a maximum temperature can be avoided when the magnetic material of the particles has a Curie temperature which is in the vicinity of the maximum permissible temperature. In the case of a temperature increase beyond the Curie temperature, the particles lose their magnetic properties, so that no reversal of the magnetization takes place in response to variation of the magnetic field and hence no further heating occurs. When the temperature drops below the Curie temperature again, the particles can be magnetized once more.

Similar effects, which can also be used for temperature control, can be observed for some ferromagnetic materials. When a so-called "comparison temperature" is reached, the magnetic field strength required for saturation drops to approximately the value zero. When this value is slightly exceeded, the necessary field strength immediately increases again. Temperature-dependent variations of the anisotropies of some magnetic particles can also be suitably used for temperature control.

The invention claimed is:

1. A method for the heating of magnetic particles which are present in a target region, which method includes the steps of
    a) generating a magnetic field whose magnetic field strength varies in space in such a manner that a first sub-region (301) having a low magnetic field strength and a second sub-region (302) having a higher magnetic field strength are formed in the target region,
    b) changing the position in space of the two sub-regions in the target region in a nonrotational manner for so long and with such a frequency that the target region is heated.

2. A method as claimed in claim 1, in which a spatially and temporally variable magnetic field is generated in order to change the position in space of the two sub-regions in the target region.

3. A method as claimed in claim 1, further comprising providing said magnetic particles as monodomain particles of a ferromagnetic material or a ferrimagnetic material.

4. A method as claimed in claim 1, further comprising providing said magnetic particles as multidomain particles of a ferromagnetic material or a ferrimagnetic material.

5. A method as claimed in claim 4, further comprising providing substrates which have dimensions in the μm range and providing a layer of a ferromagnetic soft material which is thin in comparison with said dimensions as multidomain particles on said substrates.

6. A method as claimed in claim 3, further comprising providing said monodomain particles in a colloidal dispersion.

7. A method as claimed in claim 1, further comprising enclosing particles in a molecular envelope for tissue-specific concentration.

8. A method as claimed in claim 1, further comprising heating the particles such that the temperature prevailing in the target region after the desired heating or the a maximum permissible temperature in the target region corresponds to the Curie temperature.

9. An arrangement for the heating of magnetic particles which are present in a target region, the arrangement comprising
    a) means for generating a magnetic field whose magnetic field strength varies in space in such a manner that a first sub-region (301) having a low magnetic field strength and a second sub-region (302) having a higher magnetic field strength are formed in the target region,
    b) means for changing the position in space of the two sub-regions in the target region in a nonrotational manner for so long and at such a frequency that the target region is heated.

10. An arrangement as claimed in claim 9, in which the means for generating the magnetic field include a permanent magnet arrangement for generating a magnetic gradient field whose direction is reversed in the first sub-region of the target region and which comprises a zero-crossing.

11. An arrangement as claimed in claim 9, in which the means for generating the magnetic field including a gradient coil system for generating a magnetic gradient field whose direction is reversed in the first sub-region of the target region and which comprises a zero-crossing.

12. An arrangement as claimed in claim 9, comprising means for generating a magnetic field which is superposed on the magnetic gradient field and which varies in time in order to shift the two sub-regions in the target region.

13. An arrangement as claimed in claim 9, comprising means for generating a first magnetic field and at least two further magnetic fields which are superposed on the magnetic gradient field, the first magnetic field being variable more rapidly in time and with a lower amplitude whereas the two further magnetic fields are variable more slowly in time and with a higher amplitude.

14. An arrangement as claimed in claim 13, in which the three magnetic fields extend essentially perpendicularly to one another in the target region.

\* \* \* \* \*